(12) United States Patent
Matsubara et al.

(10) Patent No.: US 6,752,960 B1
(45) Date of Patent: Jun. 22, 2004

(54) AUTOMATIC ANALYSIS APPARATUS

(75) Inventors: Shigeki Matsubara, Hitachinaka (JP);
Kyoko Imai, Hitachinaka (JP); Ryuji Tao, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 117 days.

(21) Appl. No.: 09/666,882

(22) Filed: Sep. 20, 2000

(30) Foreign Application Priority Data

Sep. 21, 1999 (JP) .......................................... 11-266656

(51) Int. Cl.⁷ .............................................. G01N 35/00
(52) U.S. Cl. ............................. 422/63; 436/47; 436/48; 422/62; 422/100
(58) Field of Search ............................. 422/63, 64, 100, 422/62; 436/47, 49, 179, 180; 73/864.01, 864.12; 134/21, 22.11, 24, 26–27, 169 R

(56) References Cited

U.S. PATENT DOCUMENTS

| | | | |
|---|---|---|---|
| 5,289,385 A | * | 2/1994 | Grandone ..................... 422/67 |
| 5,470,534 A | | 11/1995 | Imai et al. |
| 5,839,091 A | * | 11/1998 | Rhett et al. .................... 422/63 |
| 6,114,292 A | * | 9/2000 | Hoshiko et al. ........... 134/22.1 |
| 6,319,718 B1 | * | 11/2001 | Matsubara et al. ......... 422/100 |

FOREIGN PATENT DOCUMENTS

| | | |
|---|---|---|
| EP | 0-977039 | 2/2002 |
| JP | 4-169851 | 6/1992 |
| JP | 6-213906 | 5/1994 |
| JP | 6-265557 | 9/1994 |
| JP | 8-146010 | 6/1996 |
| JP | 9-281113 | 10/1997 |

* cited by examiner

*Primary Examiner*—Jill Warden
*Assistant Examiner*—Sam P. Siefke
(74) *Attorney, Agent, or Firm*—Mattingly, Stanger & Malur, P.C.

(57) ABSTRACT

An automatic analysis apparatus, in which analysis results of immunoassay analysis items are not influenced by carry-overs between samples even when the same sample container is conveyed both to a biochemical analysis unit and an immunoassay analysis unit to permit sample dispensing. The immunoassay and biochemical analysis units are arranged along a rack conveyor. A carry-over avoidance level is set on a screen every analysis item before start of an analyzing operation. When a sample given an instruction to analyze only analysis items having low carry-over avoidance levels is to be dispensed in the biochemical analysis unit, a dispenser nozzle is subjected to ordinary cleaning by water. When a sample given an instruction to analyze analysis items having high carry-over avoidance levels is to be dispensed in the biochemical analysis unit, a dispenser nozzle is cleaned with a detergent solution and water.

3 Claims, 5 Drawing Sheets

AUTOMATIC ANALYSIS APPARATUS

BACKGROUND OF THE INVENTION i) Field of the Invention

The present invention relates to an automatic analysis apparatus for analyzing organism liquid samples, and particularly to an automatic analysis apparatus provided with an analysis unit for measuring biochemical analysis items and an analysis unit for measuring, immunoassay analysis items.

ii) Description of Related Art

Analysis of organism liquid samples such as blood and urine originated from a patient has been broadly performed in order to obtain information for diagnosis of a disease nature, and automated analysis apparatuses have been used in hospitals and clinical laboratories.

A test result obtained by one automatic analysis apparatus is insufficient for the diagnosis of the disease nature in many cases, and test data needs to be collected from a plurality of analysis apparatuses in such case. An analysis system disclosed in Japanese Patent Unexamined Publication No. 281113/1997 is constituted in such a manner that a multiplicity of types of analysis items can be analyzed by one unit of system. The Japanese Patent Unexamined Publication No. 281113/1997 proposes an analysis system constituted in such a manner that a plurality of analysis units for biochemical analysis are arranged along a conveyance line of specimen racks, the specimen rack from a rack supply section is stopped at either one of the analysis units and samples on the specimen rack are dispensed by pipette nozzles.

Moreover, U.S. Pat. No. 5,470,534 discloses an analysis system constituted so as to arrange a biochemical analyzer, an immunoassay analyzer, a nucleic acid analyzer, and the like along a conveyance path of sample containers in such a manner that the same sample can be measured by the respective analyzers. In this example, it is determined in accordance with an analysis result in a first measurement stage whether or not the sample should be advanced to a second measurement stage. In the first measurement stage, biochemical analysis items are analyzed, and sample needed to be moved to the second measurement stage for determination of disease nature are analyzed by the immunoassay analyzer and/or the nucleic acid analyzer in the second measurement stage.

On the other hand, with apparatuses for automatically analyzing organism liquid samples, it is general to dispense a large number of samples in succession using one dispenser probe, so there is caused a problem that subsequent samples are contaminated by residues of preceding samples on dispenser probe. A known example for handing such carryover is disclosed, for example, in Japanese Patent Application Unexamined Publication No. 169851/1992. This publication discloses that a row of reaction containers formed on the same circumference are used to execute analysis of the biochemical analysis items for measuring components usually contained in blood, or analysis of immunoassay analysis items for utilizing aggulutination of latex particles to detect antigen and antibody.

Moreover, the Japanese Patent Unexamined Publication No. 169851/1992 describes that wasteful consumption of the cleaning liquid is eliminated by cleaning a reagent dispenser probe, having dispensed a reagent of immunoassay analysis item, with a cleaning liquid for a sufficient cleaning time or with an increased discharge amount of the cleaning liquid, and by cleaning the reagent dispenser probe, having dispensed a reagent of biochemical analysis item, for a short time or with a reduced discharge amount of the cleaning liquid. This publication also points out that even with a probe for dispensing a sample other than the reagent, the wasteful consumption of the cleaning liquid can be eliminated by adjusting a cleaning liquid flow rate.

As another type for dispensing of organism samples, use of a disposable nozzle tip is known. For example, Japanese Patent Unexamined Publication No. 146010/1996 discloses that a tip holder is provided in a movable range of a connection tube capable of connecting thereto the nozzle tip, and after one nozzle tip is conveyed to a tip holder position from a tip rack with a large number of nozzle tips arranged thereon by a movable gripper, the nozzle tip is connected to an end of the connection tube on the tip holder, and that a sample sucked into the connected nozzle tip is discharged to the reaction container, and the nozzle tip is removed from the connection tube in a tip detachment station after discharge of the sample.

Many methods of measuring immunoassay analysis items include an operation of utilizing an antigen-antibody reaction (i.e., immunoassay reaction) to connect a marker material to a solid phase. When it is necessary to analyze the immunoassay analysis items by this method, and biochemical analysis items based on a method for absorption measurement of a reacted liquid resulting from chemical reaction, it is convenient in handling of samples to arrange a plurality of analysis units in the analysis system, and to use the same sample container in common for the respective analysis units. In the U.S. Pat. No. 5,470,534 related to such analysis system, no countermeasure for avoiding a carry-over between samples is disclosed.

With the constitution of using disposable nozzle tips disclosed in the Japanese Patent Unexamined Publication No. 146010/1996, nozzle tips are replaced every sample, and so there is no possibility of influence of carry-overs between samples.

However, every sample entails the connecting operation and detaching operation of a nozzle tip, so that when a large amount of analysis items have to be treated in a short time as in biochemical analysis items, a sufficient treatment ability cannot disadvantageously be obtained.

The Japanese Patent Unexamined Publication No. 169851/1992 has proposed that the same dispenser probe for repeated use is used both for the biochemical analysis items and the immunoassay analysis items, and carry-over is avoided only by cleaning operations. However, in order to inhibit immunoassay analysis items from being affected by carry-overs between specimens from dispenser probes for biochemical analysis, cleaning time and cleaning flow rate need to be considerably increased as compared with usual cleaning with the result that the treatment ability of biochemical analysis is disadvantageously remarkably lowered.

Measurements of immunoassay analysis items such as antigen, antibody, hormone, and virus have to be detected with high sensitivity as compared with biochemical analysis items, but there is a problem that analysis result is susceptible to carry-overs between samples. Therefore, the immunoassay analysis items have a remarkably high necessity of avoiding carry-overs between samples as compared with biochemical analysis items, and so repeatedly used sample dispenser nozzles require careful handling.

SUMMARY OF THE INVENTION

It is an object of the present invention to provide an automatic analysis apparatus, which includes an immunoassay analysis unit for utilizing immunoassay reaction and a chemical analysis unit for utilizing chemical reaction, and in which even when a sample from the same sample container is dispensed to the immunoassay analysis unit after dispensing the sample to the chemical analysis unit, analysis results of analysis items given by the immunoassay analysis unit can be prevented from being influenced by carry-overs between the samples.

It is another object of the present invention to provide an automatic analysis apparatus, which gets off substantial degradation in analysis treatment ability of biochemical analysis items and can avoid carry-overs between samples at the time of analysis of immunoassay analysis items even when constituted to convey the same sample to a plurality of analysis units.

The present invention is applied to an automatic analysis apparatus including a first analysis unit for utilizing immunoassay reaction to analyze analysis objects as analysis items in a sample, a second analysis unit for measuring reaction liquids obtained by chemical reaction between the sample and reagents to analyze analysis items, analysis item indicating means for indicating analysis items being analyzed for each sample to a control unit, and a conveying device for conveying samples to at least one of a plurality of analysis units including the first and second analysis units.

In the present invention, there are provided a screen display device for displaying a screen, on which high and low levels of avoiding carry-overs between samples can be selected every analyzable analysis item, and a storage unit for storing carry-over avoidance levels selected through the screen of the screen display device in association with analysis items, and a dispenser nozzle of the second analysis unit is cleaned with water prior to a dispensing operation of a sample, for which analysis by the second analysis unit is necessary but analysis of analysis items having a high carry-over avoidance level is not instructed, and a dispenser nozzle of the second analysis unit is cleaned with a detergent solution and then with water prior to a dispensing operation of a sample, for which analyses by both the first and second analysis units is necessary and analysis of analysis items having a high carry-over avoidance level is instructed.

In a preferred embodiment of the present invention, the first analysis unit comprises a sample dispenser, which uses a dispenser tip for replacement every sample, and the second analysis unit comprises a sample dispenser, which uses a dispenser nozzle for repeated use. Also, the screen displayed by the screen display comprises an analysis item selection column, in which one or more analysis items can be selected from a plurality of analysis items, and a level selection column, in which level of avoiding carry-overs between samples can be selected with respect to the selected analysis item.

DETAILED DESCRIPTION OF THE PREFERRED EMBODIMENTS

Figure 1:
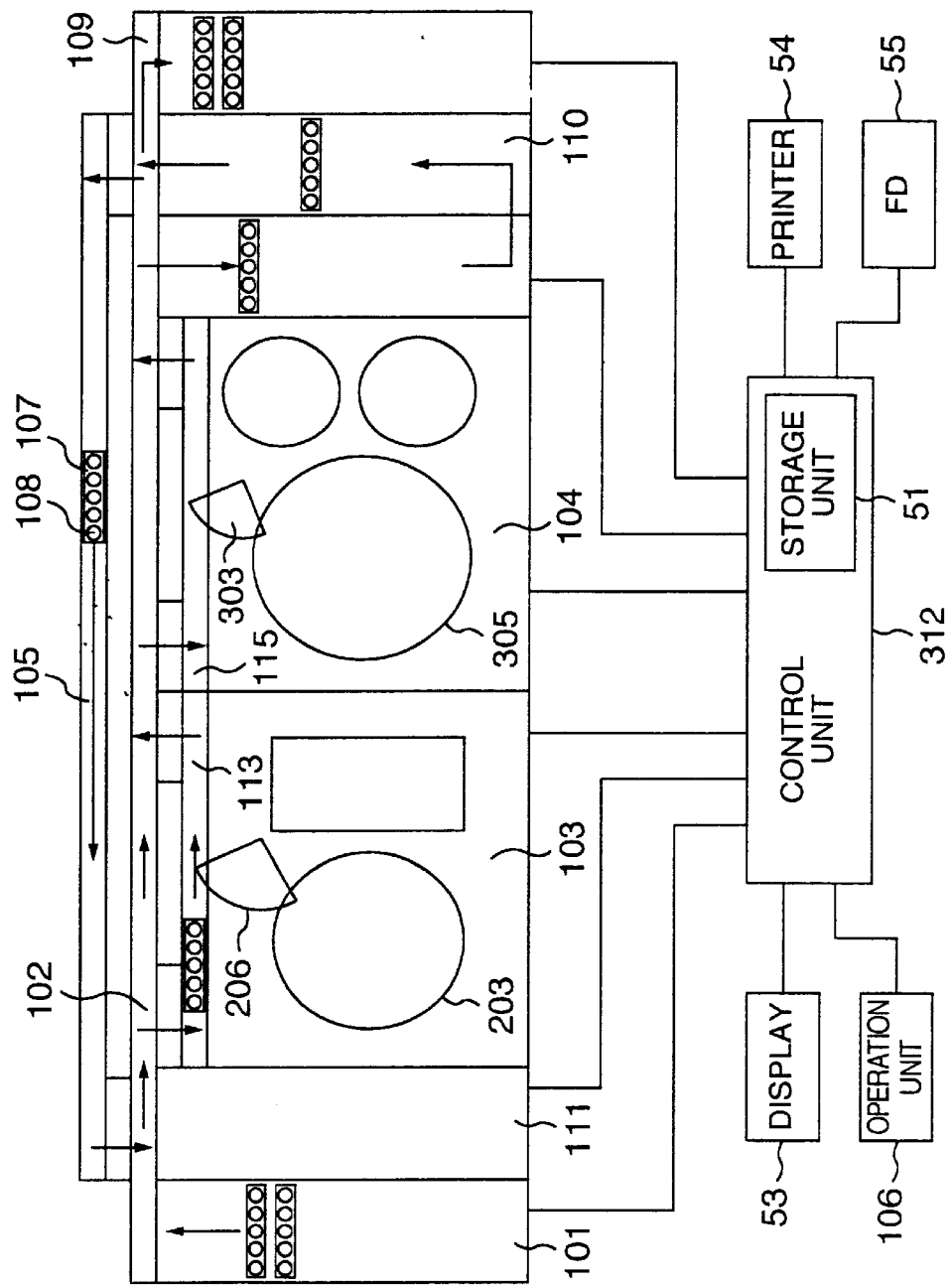
FIG. 1 is a schematic view showing an entire constitution of an automatic analysis apparatus to which the present invention is applied.

FIG. 1 is a schematic view of an entire constitution of an automatic analysis apparatus according to one embodiment of the present invention.

In FIG. 1, there is shown a conveying section 102 for conveying a rack by a belt conveyor from a specimen introducing section 101 in which a plurality of racks 107 with a plurality of sample containers 108 disposed therein can be disposed. An immunoassay analysis unit 103 and a biochemical analysis unit 104 are disposed along the conveying section 102, and a rack collecting section 109 is finally disposed. Moreover, separately from the conveying section 102, there are disposed a first standby buffer 110 and a second standby buffer 111 by which the rack 107 with the sample container 108 containing a sample requiring a retest disposed thereon is placed on standby until it is determined whether the retest is necessary or not, before the rack is conveyed to the next analysis unit or the rack collecting section 109. There is also provided a retest conveying section 105 for conveying the rack 107 to the analysis unit from the first standby buffer 110 or the second standby buffer 111 during retest.

The immunoassay analysis unit 103 and biochemical analysis unit 104 include sample dispenser pipetters 206 and 303 as sample dispensers, respectively, and the sample container 108 held in the rack 107 is conveyed together with the rack to an analysis unit sub-line 113 or 115 from the conveying section 102, and subjected to sampling in a sample suction position on the sub-line. The sample taken from the sample container by the sample dispenser pipetter 206 or 303 is discharged to a reaction container on a reaction disc 203 or 305 of each analysis unit.

Each mechanical section constituting the automatic analysis apparatus is connected to a control unit 312 consisting of a computer, and subjected to operation control at an adequate timing. The control unit 312 includes a storage unit 51, and the storage unit 51 associates and stores a level of avoiding carry-over between the samples selected through a screen of a screen display 53 with an analysis item as described later. The control unit 312 is further connected to an operation unit 106 including a keyboard, and the like, a printer 54 for printing analysis results, a floppy disk drive 55 as an external memory for storing an analysis parameter, and the like.

The items to be analyzed for a multiplicity of samples set in the specimen introducing section 101 are inputted/indicated for each sample to the control unit 312 using the operation unit 106 and screen display 53. In accordance with the analysis items indicated to be analyzed with respect to each sample, the control unit 312 judges whether the corresponding rack is to be stopped at either analysis unit, and based on the judgment result the sample is conveyed to at least one analysis unit. In the example of FIG. 1, for the sake of convenience in description, only two analysis units are shown, but three or more analysis units can be disposed along the conveying section 102.

In the embodiment of FIG. 1, the rack 107 disposed in the specimen introducing section 101 and conveyed on the conveying section 102 is first conveyed to the sample suction position of the immunoassay analysis unit 103, and after ,completion of sample dispensing in the immunoassay analysis unit 103 with respect to the sample on the rack 107, the rack 107 is conveyed to the biochemical analysis unit 104. In the automatic analysis apparatus, an operator can use the operation unit 106 and screen display 53 to set a necessity of carry-over avoidance of each analysis item before starting an analyzing operation. Accordingly, in accordance with the carry-over avoidance necessity of each analysis item set by the operator, the control unit of the analysis apparatus changes a cleaning method of the dispenser nozzle of the sample dispenser pipetter 303 of the biochemical analysis unit 104, and reduces the carry-over when the sample dispensed in the biochemical analysis unit 104 is sampled in the immunoassay analysis unit 103 for the rest of the immunoassay analysis items. Specifically, this prevents the sample in the same sample container from contacting the dispenser nozzle of the biochemical analysis unit 104 and from causing mixture with another sample residue and contamination.

Figure 4:
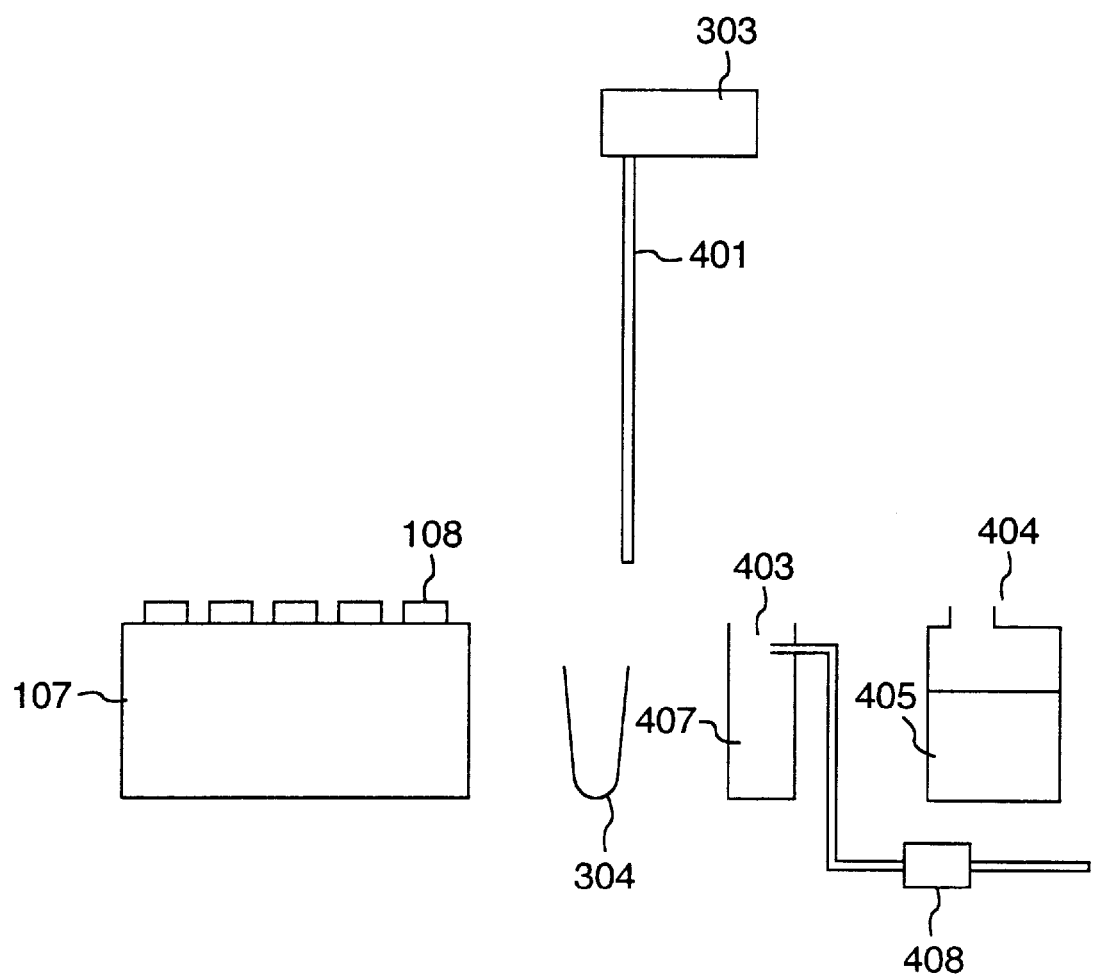
FIG. 4 is an explanatory view of a cleaning operation of a pipette nozzle in the embodiment of FIG. 1.

A cleaning operation for avoiding the carry-over between the samples will next be described with reference to FIG. 4. In FIG. 4, the sample dispenser pipetter 303 as the sample dispenser of the biochemical analysis unit 104 includes a pipette nozzle 401 as a dispenser nozzle connected to a suction/discharge pump. After each sample dispensing, the pipette nozzle 401 is cleaned by a nozzle cleaner 407 of a cleaning position 403 and repeatedly used. The pipette nozzle 401 can perform a rising/lowering operation and a revolving operation in a horizontal direction by the sample dispenser pipetter 303.

When the rack 107 is conveyed to the sample suction position, the control unit 312 judges whether or not it is instructed to analyze the analysis item selected because the sample for the next dispensing treatment has a high carry-over level between the samples. With such instruction, the sample is subjected to the dispensing treatment in the immune analysis unit 103 when a retest is necessary. Therefore, the operation of the sample dispenser pipetter 303 is controlled in such a manner that the pipette nozzle 401 is cleaned in a method different from a usual cleaning method prior to the dispensing treatment of the sample.

For the sample positioned in the sample suction position, if it is not instructed to analyze the analysis item with the high carry-over avoidance level, the sample is not dispensed in the immune analysis unit 103, and therefore the pipette nozzle 401 is cleaned only by the usual cleaning method prior to the dispensing treatment of the sample. Among a multiplicity of samples, only some samples are subjected to analysis treatment both in the biochemical analysis unit 104 and immune analysis unit 103, most of the samples require only the analysis treatment by the biochemical analysis unit in actual circumstances, and therefore the change of the cleaning method in accordance with the sample substantially fails to deteriorate analysis treatment ability of the biochemical analysis items by the biochemical analysis unit.

With respect to the first sample on the rack 107, when only the analysis item with the low carry-over avoidance level is requested to be measured, the pipette nozzle 401 lowers into the nozzle cleaner 407 in the cleaning position 403 prior to the dispensing treatment of the sample and the inside and outside of the nozzle are cleaned with water. In this case, water supplied from a cleaning water supply device 408 is sprayed to the outside of the pipette nozzle 401, and additionally by discharging water from the tip end of the pipette nozzle 401, the outer and inner surfaces of the pipette nozzle are cleaned.

Subsequently, the pipette nozzle 401 is moved onto the sample container 108 containing the first sample on the rack 107, a fixed amount of the sample in the sample container is sucked into the tip end of the pipette nozzle 401, then the nozzle is moved onto the reaction disc 305, and the sample in the pipette nozzle is discharged to a reaction container 304 on the reaction disc 305. After such sample dispensing operation, the pipette nozzle 401 is cleaned preparing for the next sample dispensing. If only the analysis item with the low carry-over avoidance level receives measurement request also with respect to the next sample, the cleaning method of the pipette nozzle is performed similarly as described above.

On the other hand, when both the analysis items with high and low avoidance levels of the carry-over between the samples receive the measurement request with respect to the sample to be next analyzed/treated, the pipette nozzle 401 is also cleaned by a detergent solution prior to the dispensing treatment of the sample. This is because the sample is taken not only in the biochemical analysis unit 104 but also in the immunoassay analysis unit 103.

Before the dispensing operation of the sample for which the analysis of the analysis items with the high carry-over avoidance level is instructed, the pipette nozzle 401 of the sample dispenser pipetter 303 of the biochemical analysis unit 104 is moved to the cleaning position 403, and lowers into the nozzle cleaner 407 so that the inner and outer surfaces of the nozzle are cleaned by water. Subsequently, the pipette nozzle 401 is moved to a detergent solution suction position 404 with a detergent solution bottle 405 placed therein by the sample dispenser pipetter 303, and the pipette nozzle 401 lowers into the detergent solution bottle to suck a predetermined amount of detergent solution into the nozzle.

With the suction, the inner and outer surfaces of the pipette nozzle 401 are brought in contact with the detergent solution and cleaned in such a manner that no residue of the former sample is carried over to the next sample. Subsequently, the pipette nozzle 401 is moved to the cleaning position 403 to discharge the sucked/held detergent solution to the nozzle cleaner 407. Subsequent to the discharge of the detergent solution, water is discharged to the nozzle cleaner 407 from the pipette nozzle 401, water from the cleaning water supply device 408 is jetted to the pipette nozzle 401, and the inner and outer surfaces of the nozzle are cleaned.

After the cleaning operation, the pipette nozzle 401 is moved onto the second sample container 108 on the rack 107 to suck the predetermined amount of sample into the nozzle, and the pipette nozzle 401 is then moved onto the corresponding reaction container 304 on the reaction disc 305 to discharge and dispense the sample sucked in the nozzle into the reaction container. The cleaning method and dispensing treatment are selectively carried out only when it is instructed to analyze the analysis items with the high carry-over avoidance level with respect to the sample to be next dispensed.

Figure 2:
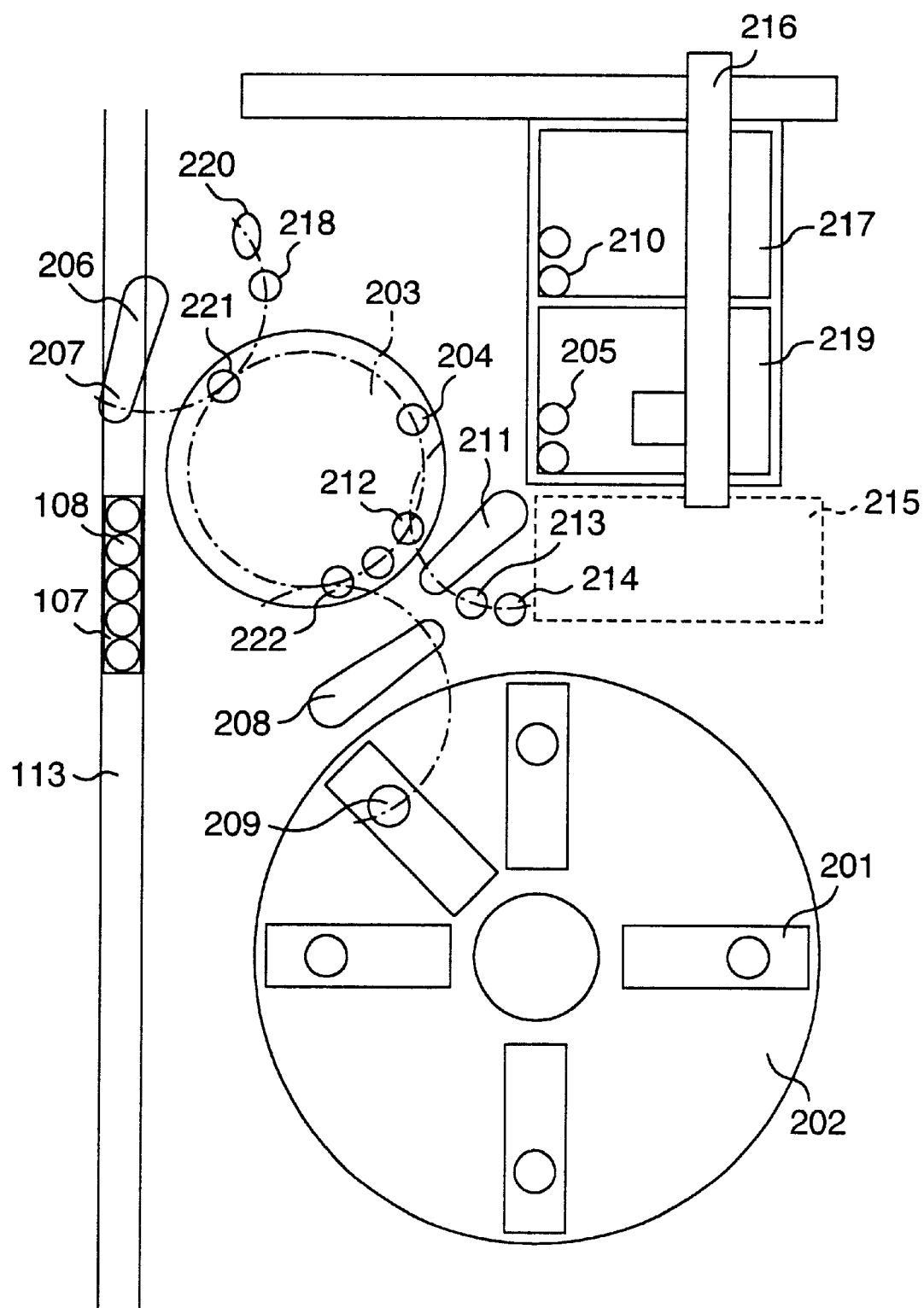
FIG. 2 is an explanatory view of a constitution example of an immunoassay analysis unit in an embodiment of FIG. 1.

A constitution example of the immunoassay analysis unit 103 will next be described with reference to FIG. 2. In FIG. 2, a plurality of reagent containers 201 containing a reagent corresponding to the analysis item analyzable by the immunoassay analysis unit are arranged on a rotatable reagent disc 202 as a reagent positioning device. A reaction disc 203 maintained at a constant temperature can rotate/operate, a plurality of reaction positions are arranged along a circumference on the reaction disc 203, and a reaction container 205 from a reaction container storage position 219 is contained. The reaction disc 203 conveys the reaction container 205 to a sample discharge position 221, reagent addition position 222 and reaction liquid suction position 212 from a reaction container set position 204 by its rotating operation.

The sample dispenser pipetter 206 can move a connection tube for connecting a disposable dispenser tip 210 to an upper part of the sample discharge position 221 from that of a sample suction position 207 in a horizontal direction. Moreover, vertical movement is also possible in the respective positions. The disposable dispenser tip 210 is attached to a end of the tip connection tube of the sample dispenser pipetter 206 in a tip connection position 218 prior to sample suction.

A reagent dispenser pipetter 208 can move between the upper part of a reagent suction position 209 on the reagent disc 202 and the upper part of the reagent addition position 222. Moreover, vertical movement is also possible in the respective positions. A shipper 211 can move among the upper part of the reaction liquid suction position 212, the upper part of a buffer liquid suction position 213 and the upper part of a cleaning liquid suction position 214 for a flow cell, and can also move vertically in the respective positions. Moreover, the shipper 211 has a function of feeding a reaction liquid to the flow cell in a detection unit 215 via a tube. A tip and reaction container conveyance mechanism 216 which can move a gripper in x and y directions convey the disposable dispenser tip 210 to the tip connection position 218 from a tip storage position 217, and convey the disposable reaction container 205 to the reaction container set position 204 from the reaction container storage position 219. For the reagent dispenser pipetter 208 and shipper 211, nozzle outer walls are cleaned with water in the corresponding cleaning position.

A flow of treatment in the immunoassay analysis unit 103 will next be described. First, the tip and reaction container conveyance mechanism 216 convey the disposable dispenser tip 210 to the tip connection position 218, and subsequently convey the reaction container 205 to the reaction container set position 204. The rack 107 holding the sample container 108 is conveyed on the sub-line 113 in such a manner that the sample container 108 containing the sample to be analyzed is positioned in the sample suction position 207. Additionally, the reagent disc 202 rotates in such a manner that the reagent container 201 containing the reagent for use in the analysis is positioned in the reagent suction position 209. Simultaneously the reagent dispenser pipetter 208 moves to the upper part of the reagent suction position 209. In the reagent suction position 209 the reagent dispenser pipetter 208 lowers to suck the reagent into the pipette nozzle. Subsequently, the reagent dispenser pipetter 208 rises and moves to the nozzle cleaning position. When the pipette nozzle reaches the upper part of the nozzle cleaning position, cleaning water is blown out of a cleaning tank to clean the tip end of the pipette nozzle.

On the other hand, the sample dispenser pipetter 206 moves the dispenser tip 210 to the upper part of the sample suction position 207, lowers into the sample container 108 on the rack 107, and sucks the predetermined amount of sample. After sample suction, the dispenser tip rises and moves to the sample discharge position 221. Subsequently, the dispenser chip lowers and discharges the sample sucked/held in the dispenser tip into the reaction container 205. After the sample is discharged, the sample dispenser pipetter 206 raises the dispenser tip and moves to a tip discard position 220. In the tip discard position 220 the sample dispenser pipetter 206 removes and discards the disposable dispenser tip 210 from the connection tube.

After a predetermined time required for reaction elapses, the shipper 211 moves a suction nozzle to the upper part of the buffer liquid suction position 213, and lowers the nozzle to suck the buffer liquid toward the flow cell through the nozzle. Thereafter, the tip end of the nozzle of the shipper 211 is cleaned in the nozzle cleaning position.

Subsequently, the reaction disc 203 conveys the reaction container 205 to the reaction liquid suction position 212. In the reaction liquid suction position 212, the shipper 211 sucks the reaction liquid toward the flow cell through the nozzle. After the reaction liquid is sucked, the shipper 211 moves the nozzle to the buffer liquid suction position 213 to suck the buffer liquid. The sucked buffer and reaction liquids are fed to the flow cell in the detection unit 215 through the nozzle, and measurement is performed. Subsequently, the shipper 211 moves the nozzle to the cleaning liquid suction position 214, the cleaning liquid for the flow cell is sucked, and the inside of the flow cell in the detection unit 215 is cleaned by the cleaning liquid.

Figure 3:
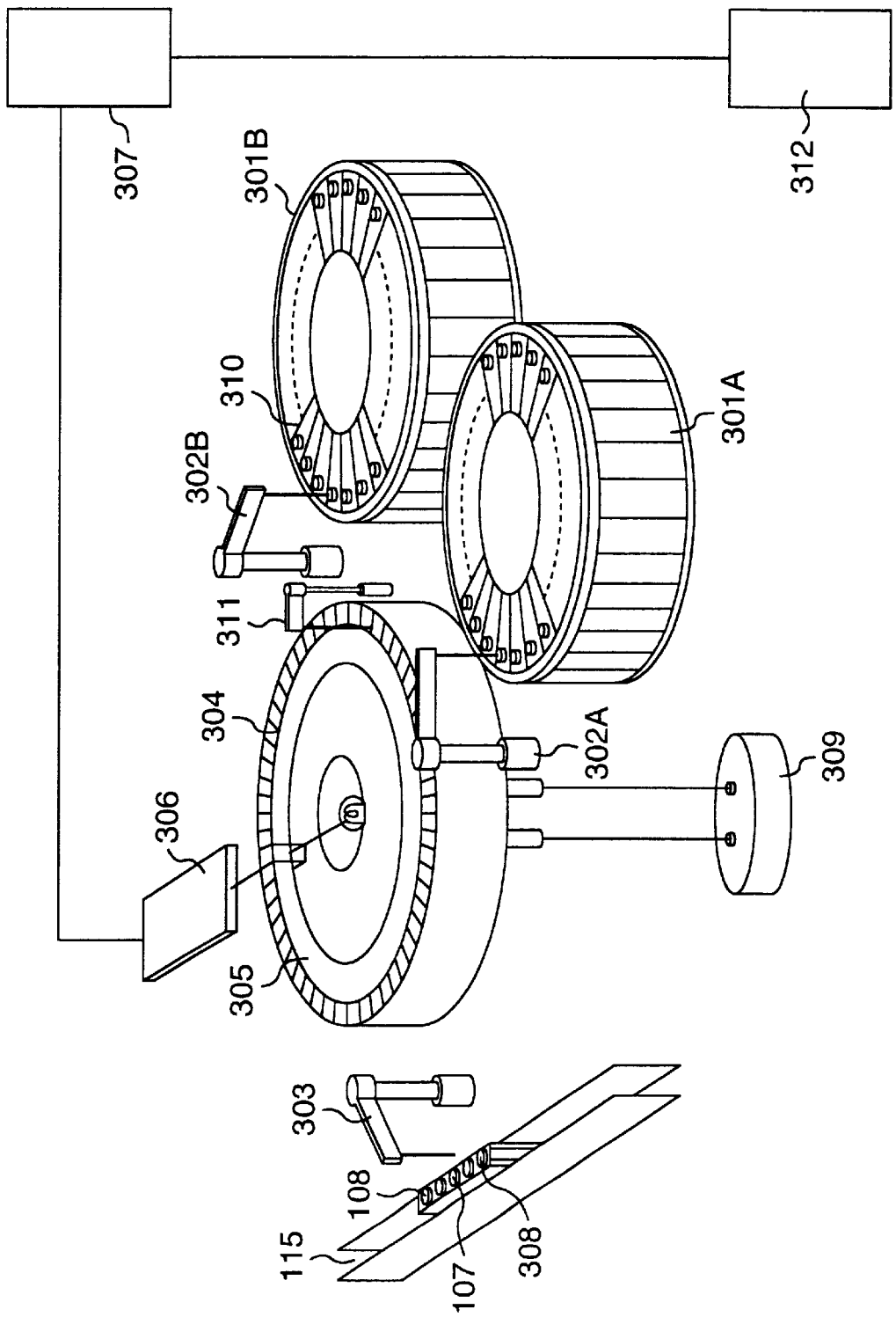
FIG. 3 is an explanatory view of a constitution example of a biochemical analysis unit in the embodiment of FIG. 1.

A constitution example of the biochemical analysis unit 104 will next be described with reference to FIG. 3. In FIG. 3, the biochemical analysis unit 104 is provided with: a reagent supply system including reagent discs 301A, 301B for holding a multiplicity of reagent containers 310 and reagent dispenser pipetters 302A, 302B; a sample supply system including the sample dispenser pipetter 303; a reactor including the reaction disc 305 for holding a multiplicity of reaction containers 304; and a measurement system including a multiple-wavelength photometer 306 and an analog/digital converter 307.

In FIG. 3, the rack 107 for holding the sample container 108 is conveyed to a sample suction position 308 on the sub-line 115 from the conveying section 102. The sample dispenser pipetter 303 sucks the predetermined amount of sample in the sample container 108 into the pipette nozzle 401 to discharge the sample into the reaction container 304.

The reaction container 304 to which the sample liquid is discharged/dispensed is moved to a first reagent addition position by rotation of the reaction disc 305 whose temperature is kept by a constant temperature tank 309. In this case, the reagent disc 301A is also moved so that the reagent container 310 for the analysis item of the sample having reached the reagent addition position by rotation operation is positioned in the reagent suction position. Subsequently, a predetermined first reagent sucked in the pipette nozzle of the reagent dispenser pipetter 302A is added to the reaction container 304 moved to the first reagent addition position. After addition of the first reagent the reaction container 304 is moved to a position of an agitator 311, and first agitation is performed. With the analysis item requiring the addition of a second reagent, the second reagent is further added by the reagent dispenser pipetter 302B, and content is agitated.

The reaction container 304 containing a reaction liquid obtained by mixing the sample and reagent is conveyed to cross a light flux from a light source, and light transmitted through the reaction container is incident upon the multiple-wavelength photometer 306. Subsequently, absorbency of the reaction liquid as a content of the reaction container 304 is detected by the multiple-wavelength photometer 306. A detected absorbency signal is supplied to the analog/digital (A/D) converter 307 and the control unit 312 consisting of the computer via an interface, and converted to density of the analysis item as a measurement object in the sample. After completion of the analysis/measurement the reaction container 304 is moved to a position of a reaction container cleaning mechanism (not shown), cleaned with water by the reaction container cleaning mechanism after discharge of the reaction liquid from the reaction container, and used for the next analysis.

An example for setting the carry-over avoidance level in the embodiment of FIG. 1 will next be described with reference to FIG. 5. Before start of the analyzing operation, the analysis items required for each sample originated from a patient are inputted through the operation unit 106. For each sample, usually a plurality of analysis items are requested to be analyzed/tested. In this automatic analysis apparatus, the analysis items with a high carry-over avoidance necessity of the sample are predetermined, and stored in the storage unit 51 of the control unit 312.

When the operation unit 106 gives an instruction to set analysis conditions, an analysis condition setting screen 70 is displayed on the screen display 53 consisting of CRT, and the like. In the screen 70, as shown in FIG. 5, disposed above are a routine operation screen call button 71, a reagent management screen call button 72, a calibration screen call button 73, a precision management screen call button 74, and a utility screen call button 75. By pushing each button with fingers by a touch panel system, or operating a mouse or the like to click a pointer, the corresponding screen is displayed in a middle portion. FIG. 5 shows an example in which the utility screen call button 75 is operated to call the corresponding screen. A help button 76 is disposed in the bottom of the analysis condition setting screen 70, and explanation for screen operation is displayed by operating the button.

Moreover, in either one of left and right areas of the analysis condition setting screen 70, a stop instruction button 81 of the analysis apparatus, a stop instruction button 82 of a sampling operation during the analyzing operation, a call button 83 of an alarm screen, a call button 84 of a screen indicating conveyance states of the respective analysis units and racks, a printing instruction button 85 to the printer 54, a start instruction button 86 of the analysis apparatus, and the like are disposed. The respective buttons are always displayed while the analysis condition setting screen 70 is displayed.

Now, when the utility screen call button 75 is selected, in a display area 150, respective screen call buttons of system 151, maintenance 152, application 153, calculation item 154, carry-over 155, report 156, and unit constitution 157 appear. Additionally, an addition instruction button 161, a write instruction button 162 of database to the floppy disk memory, an erase instruction button 163, and a read instruction button 164 from the floppy disk storage unit appear. In this state, when the application screen call button 153 is selected, a list 170 indicating a plurality of analysis items and sample types appears, and additionally detailed screen call buttons 171 to 174 appear.

Figure 5:
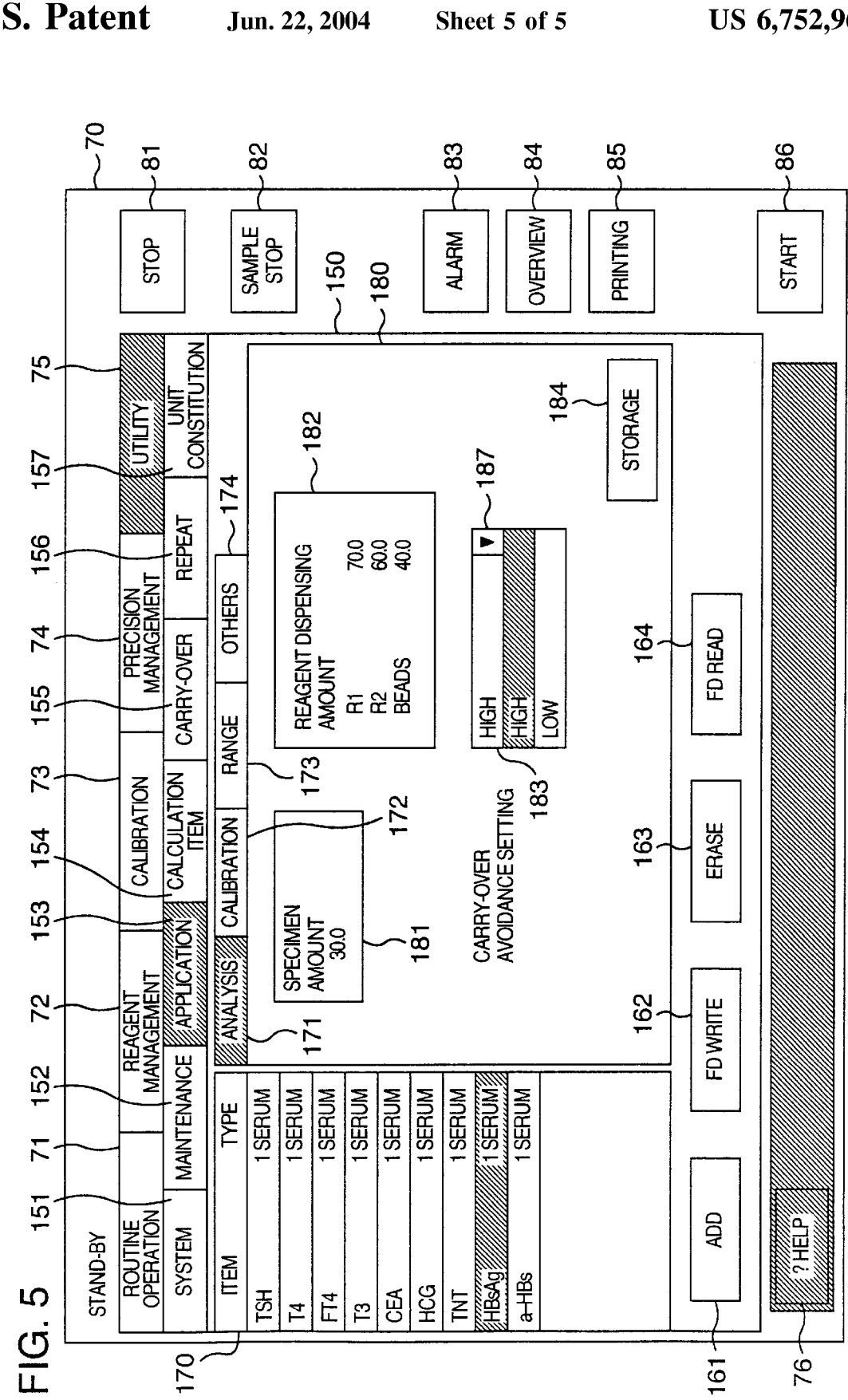
FIG. 5 is an explanatory view showing an example of a screen for setting a level of avoiding carry-over between the samples in the embodiment of FIG. 1.

Furthermore, when the analysis button 171 is selected from the detailed screen call buttons, the screen appears in a display area 180 as shown in FIG. 5. Specifically, a specimen amount setting column 181, a reagent dispensing amount setting column 182, a setting column 183 of the carry-over avoidance level between the samples and a storage instruction button 184 are displayed.

In the screen of FIG. 5, for the analysis items displayed in the list 170, TSH denotes thyroid-stimulating hormone (thyrotropin), T4 denotes thyroxine, FT4 denotes free thyroxine, T3 denotes tri-iodothyronine, CEA denotes carcino-embryonic antigen, HCG denotes human chorionic gonadotropin, TNT denotes troponin T, HBsAg denotes hepatitis B surface antigen, and a-HBs denotes antibody of hepatitis B surface antigen. Additionally, these are all immunoassay analysis items.

It is now assumed that HBsAg is selected from the analysis items of the list 170, 30 $\mu$l is inputted as a sampling amount in the specimen amount setting column 181, and 70 $\mu$l as an addition amount of a first reagent R1, 60 $\mu$l as the addition amount of a second reagent R2, and 40 $\mu$l as the addition amount of a bead reagent are inputted in the reagent dispensing amount setting column 182. Moreover, "high" level is selected/indicated from "high" and "low" in the carry-over avoidance level setting column 183. The selection of the high or low level is performed by a level selection button 187. Subsequently, when the storage instruction button 184 is selected, with respect to the analysis item of HBsAg, together with the specimen amount and reagent dispensing amount, the avoidance level of carry-over between the samples are associated with the analysis item, indicated, and stored in the storage unit 51.

Subsequently, by selecting another analysis item displayed in the list 170 and similarly setting the specimen amount, reagent dispensing amount, and carry-over avoidance level in accordance with the corresponding item, these conditions can successively be set. Moreover, when a plurality of analysis items are selected from the list 170, and the common carry-over avoidance level can be indicated, the carry-over avoidance level can collectively be indicated with respect to a plurality of analysis items.

In the carry-over avoidance level setting column 183, with the "high" level, sampling is performed on condition that there is no carry-over between the samples. Concretely, the general control unit 312 controls a conveyance destination of the corresponding specimen rack in such a manner that in the immunoassay analysis unit 103 the sampling is executed by the dispenser using the disposable dispenser tip replaced with a new tip for each sample. Furthermore, in the biochemical analysis unit 104, control is performed in such a manner that the dispenser nozzle for sampling is cleaned by the cleaning method different from the usual cleaning method for only the biochemical analysis item, prior to dispensing of the sample with the high level designated thereto. With indication of the "high level" with respect to a specified analysis item, the storage unit 51 stores the specified analysis item which requires the dispensing by the disposable dispenser tip. On the other hand, the "low" level indicates that the sampling may be executed using only the dispenser provided with the dispenser nozzle cleaned and repeatedly used for a large number of samples, and the corresponding analysis item can be subjected to analysis/measurement in the biochemical analysis unit 104 in FIG. 1.

The analysis conditions set by the setting screen as shown in FIG. 5 are continuously used in accordance with the respective analysis items as long as no condition is changed afterwards. Therefore, when a request for test of a patient sample is made, and the analysis item is inputted, the analysis conditions set in FIG. 5 are automatically applied.

In this manner, in the analysis apparatus of FIG. 1, there is particularly a necessity of carry-over avoidance between the samples. Specifically, for the analysis item with the indication of the "high" level, indicated information is stored in the storage unit. Moreover, when the same analysis item as the already indicated analysis item is selected through the analysis condition setting screen 70 for later setting of new analysis condition, operation is performed in such a manner that the stored information, that is, the information indicating the necessity of carry-over avoidance is outputted to the display. In the example of FIG. 5, when the analysis item is selected, "high" is displayed in the setting column 183.

According to the present invention, with respect to the sample to which the measurement request for the analyses both by the chemical analysis unit and immunoassay analysis unit is made, there is a possibility that after the sample dispensing to the chemical analysis unit, the immunoassay analysis item remarkably susceptible to the influence of the carry-over between the samples as compared with the biochemical analysis item is sampled from the same sample container in the immunoassay analysis unit. In this case, by cleaning the dispenser nozzle with detergent and water prior to the sample dispensing to the chemical analysis unit, an effect is produced that the analysis result of the immunoassay analysis item fails to be influenced by the carry-over between the samples.

What is claimed is:

1. An automatic analysis apparatus, comprising:

a first analysis unit, provided with a sample dispenser nozzle, for utilizing immunoassay reactions to analyze analysis objects as analysis items in a sample, a second analysis unit, provided with a sample dispenser nozzle, for measuring reaction liquids obtained by chemical reaction between the sample and reagents to analyze analysis items, analysis item indicating means for indicating analysis items to be analyzed for each sample to a control unit, a conveying device for conveying samples to at least one of a plurality of analysis units including the first and second analysis units, a screen display device for displaying a screen, on which one of higher and lower levels of avoiding carry-overs between samples is selected for every individually analyzable analysis item, and a storage unit for storing carry-over avoidance levels selected through the screen of the screen display device in association with analysis items, means for cleaning said sample dispenser nozzle wherein selection of an analysis item having the higher level of avoiding carry-over controls said means for cleaning said sample dispenser nozzle of said second analysis unit to clean said sample dispenser nozzle with water after being cleaned with a detergent solution, and wherein selection of an analysis item having the lower level of avoiding carry-over controls said means for cleaning said sample dispenser nozzle of the second analysis unit to clean said sample dispenser nozzle with water excluding a detergent solution.

2. The automatic analysis apparatus according to claim 1, wherein said first analysis unit comprises a sample dispenser, which uses a dispenser tip for replacement every sample, and said second analysis unit comprises a sample dispenser, which uses a dispenser tip for repeated use.

3. The automatic analysis apparatus according to claim 1, wherein the screen displayed by said screen display comprises an analysis item selection column, in which one or more analysis items can be selected from a plurality of analysis items, and a level selection column, in which the levels of avoiding carry-over between samples is selected with respect to the selected analysis item.

* * * * *